(12) United States Patent
Shimosoyama et al.

(10) Patent No.: US 11,382,839 B2
(45) Date of Patent: Jul. 12, 2022

(54) ION SUSTAINED-RELEASE DENTAL HYDRAULIC TEMPORARY SEALING MATERIAL COMPOSITION

(71) Applicant: KABUSHIKI KAISHA SHOFU, Kyoto (JP)

(72) Inventors: Shun Shimosoyama, Kyoto (JP); Kumiko Marunishi, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 0 days.

(21) Appl. No.: 15/834,875

(22) Filed: Dec. 7, 2017

(65) Prior Publication Data

US 2018/0161250 A1 Jun. 14, 2018

(30) Foreign Application Priority Data

Dec. 9, 2016 (JP) .............................. JP2016-239224

(51) Int. Cl.
| | | |
|---|---|---|
| *A61K 6/00* | (2020.01) | |
| *A61Q 11/00* | (2006.01) | |
| *A61K 6/77* | (2020.01) | |
| *A61K 8/21* | (2006.01) | |
| *A61K 6/17* | (2020.01) | |
| *A61K 6/19* | (2020.01) | |
| *A61K 6/858* | (2020.01) | |
| *A61K 6/887* | (2020.01) | |

(52) U.S. Cl.
CPC .................. *A61K 6/77* (2020.01); *A61K 6/17* (2020.01); *A61K 6/19* (2020.01); *A61K 6/858* (2020.01); *A61K 6/887* (2020.01); *A61K 8/21* (2013.01); *A61Q 11/00* (2013.01)

(58) Field of Classification Search
CPC .. A61K 2300/00; A61K 33/06; A61K 8/8164; A61K 8/8152; A61K 6/54; A61K 6/30; A61K 6/77; A61K 6/80; A61K 6/00; A61K 6/858; A61K 6/884; A61K 6/20; A61K 6/889; A61K 6/35; A61K 8/69; A61K 6/836; A61K 6/71; A61K 45/06; A61K 6/50; A61P 17/02; A61L 31/127; A61Q 11/00
See application file for complete search history.

(56) References Cited

U.S. PATENT DOCUMENTS

| | | | |
|---|---|---|---|
| 5,051,130 A * | 9/1991 | Futami | A61K 6/0088 106/35 |
| 6,284,030 B1 | 9/2001 | Orlowski et al. | |
| 2003/0050359 A1* | 3/2003 | Kimura | A61K 6/0023 522/182 |
| 2005/0020720 A1* | 1/2005 | Dickens | A61K 6/0017 523/115 |
| 2010/0292359 A1* | 11/2010 | Yamamoto | A61K 6/0017 522/78 |
| 2011/0070563 A1* | 3/2011 | Ori | A61K 6/0038 433/224 |
| 2011/0244431 A1 | 10/2011 | Shinozaki et al. | |
| 2015/0342840 A1 | 12/2015 | Sadakane et al. | |
| 2017/0014312 A1* | 1/2017 | Suzuki | A61K 6/0023 |

FOREIGN PATENT DOCUMENTS

| | | |
|---|---|---|
| IE | 70752 B1 * | 12/1996 |
| JP | 38-2628 | 3/1963 |
| JP | 02144069 A * | 6/1990 |
| JP | H04317656 A * | 11/1992 |
| JP | 2011-213608 | 10/2011 |
| JP | 2013-40137 | 2/2013 |
| JP | 2015-227308 | 12/2015 |
| WO | WO-2014111255 A1 * | 7/2014 ........... A61K 6/0008 |

OTHER PUBLICATIONS

ScienceLab.com. Glycerin MSDS. Date retrieved: Aug. 9, 2018. <http://www.sciencelab.com/msds.php?msdsId=9927350>. (Year: 2018).*
Extended European Search Report dated May 9, 2018 in European Application No. 17205165.8.
Office Action dated Apr. 21, 2020 in corresponding Japanese Patent Application No. 2016-239224 with English language translation.

* cited by examiner

*Primary Examiner* — Tracy Liu
(74) *Attorney, Agent, or Firm* — Wenderoth, Lind & Ponack, L.L.P.

(57) ABSTRACT

The present invention provides a dental hydraulic temporary sealing material composition on which a protection of tooth substance, such as tooth substance strengthening and control of secondary dental caries, can be expected by sustained-releasing various ions including a fluoride ion, while having a high initial setting ability. More specifically, the present invention provides a dental hydraulic temporary sealing material composition comprising 65.0% to 85.0% by mass of component (1): a hydraulic inorganic powder; 10.0% to 25.0% by mass of component (2): an organic solvent; 3.0% to 15.0% by mass of component (3): a resin; and 0.01% to 10.0% by mass of component (4): an ion sustained-release glass.

10 Claims, 2 Drawing Sheets

ION SUSTAINED-RELEASE DENTAL HYDRAULIC TEMPORARY SEALING MATERIAL COMPOSITION

TECHNICAL FIELD

The present invention relates to a dental hydraulic temporary sealing material composition having an ion sustained releasability. More specifically, the present invention relates to a dental hydraulic temporary sealing material composition which is excellent for an initial setting ability and also has a preventive function due to a sustained release of various ions including a fluoride ion.

BACKGROUND ART

When a tooth substance in a mouth is obliged to be deleted partially due to dental caries, etc., a direct restoration which restores the deletion portion of the tooth substance by using a filling material such as a composite resin for dental filling, an indirect restoration in which a prosthesis device is produced to reproduce a crown form to bind the device to the deletion part of the tooth substance by using a dental cement, or the like has been generally performed. Moreover, when dental caries progress until a deep dentine and a bacterial infection is found in a dental pulp or root canal and the like, a root canal therapy such as pulpectomy treatment, removal of an infected tooth substance, etc., is performed. In these treatments, a temporary seal which temporarily blocks cavities and root canals by using a temporary filling material called as a dental temporary sealing material has been performed for the purpose of preventing a contamination of foods into cavities or root canals or a bacterial infection of a treatment site, blocking drugs filled into root canals, and the like until preparing the prosthesis device, in a follow-up observation period after pulpectomy or removal of an infected tooth substance, or during a drug application period.

From such background, the dental temporary sealing material needs a good sealability. Moreover, since there is a possibility that sealability may be lacked when a filled temporary sealing material is moved or transformed by a masticatory movement, etc., after the treatment, it is also an important requirement to set it early within the mouth. On the other hand, the dental temporary sealing material must be able to be removed easily without damaging tooth substance around its application site circumference since the dental temporary sealing material is a material to be removed during the treatment process.

Examples of the dental temporary sealing material include a temporary stopping comprising a thermoplastic resin, a dental cement such as eugenol cement, non-eugenol cement, and zinc phosphate cement, a dental resin temporary sealing material comprising a polymerizable monomer and a polymerization initiator, a hydraulic temporary sealing material containing calcium sulfate as a main component.

The temporary stopping is used by heating when using to soften its material and to be filled in cavities. There is a problem that sealability of cavities is poor since its filling or removing is easy whereas heating and softening operation is necessary each time upon using, and thereby it is not only accompanied with a complicated process, but also its shrinkage at the time of cooling and setting is large.

The dental cement is filled and used by mixing a powder material and a liquid material to make them paste form. Since there are few dimensional changes at the time of setting as compared with the temporary stopping, the sealability of cavities is good. However, the mixing of the powder material and the liquid material is not only complicated, but also needs skills. Moreover, since the set substance is hard, there is also a problem that its removal is difficult.

The dental resin temporary sealing material is cured by a polymerization reaction of polymerizable monomers, it includes a chemical polymerization type in which the dental resin temporary sealing material is polymerized and cured by mixing powder materials and liquid materials, and a photopolymerization type in which the dental resin temporary sealing material is polymerized and cured by light-irradiating a composition comprising a photopolymerization initiator to be excited with a specific wavelength light. Since these are quickly cured when its polymerization reaction starts, there is an advantage capable of being able to function early after a treatment. However, since these are accompanied with polymerization shrinkage at the time of setting, there is a defect that their sealability is poor.

On the one hand, since the hydraulic temporary sealing material is set by reacting with moisture such as saliva in a mouth by filling a putty-like paste into cavities, its operativity is excellent without need of heating, mixing, or light-irradiating. Moreover, since the main component calcium sulfate has a property in which it expands accompanying with setting, its sealability of cavities is also excellent.

Japanese Patent Publication No. S38-2628 (Patent Document 1) discloses a hydraulic temporary sealing material comprising 10 to 35% by weight of vinyl acetate, vinyl chloride or a copolymer of the both, 1 to 10% by weight of ethyl alcohol, 1 to 10% by weight of glycol acetate, 5 to 30% by weight of zinc sulfate cement, and 30 to 65% by weight of calcined plaster. There is disclosed that the hydraulic temporary sealing material is well adhered to cavities, and can be removed easily by an excavator, etc. upon removing the sealing material from a tooth. However, there is a defect that a time to set it after filling in cavities is long. Patients especially have to notice biting strongly a part filled with the hydraulic temporary sealing material for approximately 1 hour after filling since the material has a slow setting ability (initial setting ability) immediately after filling.

Japanese Patent Publication No. 2011-213608 (Patent Documents 2) discloses a hydraulic temporary sealing material comprising A) 10 to 90% by weight of calcium sulfate, B) 5 to 40% by weight of a vinyl acetate resin, C) 1 to 40% by weight of an inorganic filler, D) 1 to 30% by weight of an alcohol having a boiling point of 110° C. or more, and E) 0.001 to 5% by weight of a nonion surfactant. This hydraulic temporary sealing material adheres without moisture of a tooth surface being repelled on the paste surface by hydrophilic action of an organic solvent having a moderate hydrophilic property and a nonion surfactant. Initial setting ability can be enhanced by permeating and spreading moisture to the inside of the paste more early and stably according to its effect. Further, since the effect on the hydrophilic property is also effective in adhesiveness with a tooth substance, the filling property in the mouth becomes good, and in those results, there is disclosed that its sealability is enhanced. However, the initial setting ability was not still enough, and thereby there was a need for its improvement.

Since removability is an important requirement for dental temporary sealing materials as discussed above, neither of those temporary sealing materials also provide bonding to a tooth substance. That is, in an indirect restoration, it is necessary to remove the temporary sealing material upon mounting a prosthesis device, and in a root canal therapy, the temporary sealing material is once removed at the time of follow-up observation to check its grade of recovery, or an additional application of drugs may be performed. From this reason, if the temporary sealing material has the bonding to the tooth substance, the bonding interface of the temporary sealing material and tooth substance must be deleted by means of a dental turbine, etc., and thereby a tooth substance which needs not to be essentially deleted will lose simultaneously. It may provide not only an aggravation of workability, but also a harmful influence on a fitting of prosthesis, and there is a possibility that a dental life may be impaired by unnecessary deletion of a remaining tooth substance. Therefore, this is not desirable from a viewpoint of a long-term mouth protection.

Since none of the dental temporary sealing materials provide bonding over tooth substance by considering that their removability is important as discussed above, a perfect sealability would not be able to be expected. From this reason, there is concern over contamination of foods or a bacterial invasion, etc. in a gap between the tooth substance and the temporary sealing material, and further leakage of drugs in the root canal therapy. When such risk is realized, there is a possibility of causing generation of secondary dental caries by invaded bacteria, reinfection of a root canal, etc.

Thus, the temporary sealing material needs good removability and an opposite property of the high sealability for tooth substance protection, and the conventional temporary sealing materials have held the dilemma by these needs.

REFERENCE DOCUMENTS

Patent Documents

Patent Document 1: Japanese Patent Publication No. S38-2628 B
Patent Document 2: Japanese Patent Publication No. 2011-213608 A

SUMMARY OF THE INVENTION

Problems to be Solved by the Invention

Since the conventional hydraulic temporary sealing materials had slow initial setting ability, there is a defect that it cannot function early after a treatment. Further, there is concern over generation of the secondary dental caries by invaded bacteria into cavities or root canals, etc. Therefore, a problem of the present invention is to provide a dental hydraulic temporary sealing material composition on which the protection of tooth substance, such as tooth substance strengthening and prevention of secondary dental caries can be expected by various ions including a fluoride ion, while having a high initial setting ability.

Means for Solving the Problems

The present inventors intensively studied the above-mentioned problems to solve them. As a result of the study, the inventors found out that in a hydraulic composition comprising a hydraulic inorganic powder, an organic solvent and a resin, an addition of an ion sustained-release glass provides a sustained-release ability of various ions including a fluoride ion, and combination of each component at a specific rate results in a well-balanced expression of an excellent initial setting ability and a high sustained-release ability of various ions including a fluoride ion, and thereby the inventors accomplished the present invention.

Namely, the present invention is a dental hydraulic temporary sealing material composition comprising,
65.0% to 85.0% by mass of component (1): a hydraulic inorganic powder;
10.0% to 25.0% by mass of component (2): an organic solvent;
3.0% to 15.0% by mass of component (3): a resin; and
0.01% to 10.0% by mass of component (4): an ion sustained-release glass.

Moreover, the component (4): ion sustained-release glass preferably sustained-releases at least a fluoride ion, more preferably sustained-releases a fluoride ion and further sustained-releases one or more kinds of bivalent to tetravalent ions, still more preferably sustained-releases at least a fluoride ion and further sustained-releases one or more kinds of strontium ion, aluminum ion, and borate ion, and most preferably sustained-releases at least a fluoride ion, a strontium ion, and a borate ion.

It is also preferred that the component (1): hydraulic inorganic powder is calcium sulfate.

It is also preferred that the component (2): organic solvent is glycerin or a derivative thereof.

It is also preferred that the component (3): resin comprising at least one kind of a homopolymer of vinyl acetate or vinyl chloride, and a copolymer thereof.

Effects of the Invention

Since the ion sustained-release dental hydraulic temporary sealing material composition of the present invention has a good initial setting ability immediately after application in the mouth, it can function early. Strengthening of the tooth substance is also expectable by a sustained release of various ions including a fluoride ion, and even if a defect occurs on sealability, it is expectable to preventing generation of the secondary dental caries.

MODES FOR CARRYING OUT THE INVENTION

The present invention relates to an ion sustained-release dental hydraulic temporary sealing material composition comprising, 65.0% to 85.0% by mass of component (1): a hydraulic inorganic powder; 10.0% to 25.0% by mass of component (2): an organic solvent; 3.0% to 15.0% by mass of component (3): a resin; and 0.01% to 10.0% by mass of component (4): an ion sustained-release glass.

The component (1): hydraulic inorganic powder is an inorganic powder which is reacted and set in the presence of water, and the component (1) is a component which provides setting ability to the ion sustained-release dental hydraulic temporary sealing material composition of the present invention.

Known inorganic powders may be used as the component (1): hydraulic inorganic powder without any restrictions as long as the component (1) is an inorganic powder which is reacted and set in the presence of water.

By illustrating the component (1): hydraulic inorganic powder, its specific examples include calcium sulfate, calcium silicate, calcium aluminate, hydraulic alumina, and portland cement, and calcium sulfate among them is preferably used. Examples of calcium sulfate include α-hemihydrate gypsum and β-hemihydrate gypsum. These hydraulic inorganic powders may be used in a combination of two or more kinds.

Although the particle size of the component (1): hydraulic inorganic powder is not limited, it preferably ranges from 0.01 μm to 100 μm, more preferably from 0.1 μm to 50 μm. The shape of the component (1): hydraulic inorganic powder is not in particular limited, and any shapes such as spherical, needle-like, platy, crushed, and scaly may be used.

It is preferred that the component (1): hydraulic inorganic powder is preferably contained at 65.0% to 85.0% by mass, more preferably 70.0% to 80.0% by mass, still more preferably 70.0% to 76.0% by mass, and most preferably 71.0% to 76.0% by mass based on the total mass of the ion sustained-release dental hydraulic temporary sealing material composition. When the content of the component (1) is less than 65.0% by mass, its initial setting ability may be reduced. When the content of the component (1) exceeds 85.0% by mass, a paste before setting will become very hard, and its operativity will not only worsen upon filling into cavities or root canals, but also the ion sustained-release dental hydraulic temporary sealing material composition of the present invention may not be able to be made into a paste form.

The component (2): organic solvent is a component for preparing a paste of the ion sustained-release dental hydraulic temporary sealing material composition of the present invention.

The component (2): organic solvent is a liquid at normal temperature, and known organic solvents may be used without any restrictions as long as it does not react with the component (1): hydraulic inorganic powder. Provided that an organic solvent with low volatility is preferably used from a viewpoint of preservation stability.

By illustrating the component (2): organic solvent, its specific examples include alcohols such as methanol, ethanol, propanol, isopropyl alcohol, isobutyl alcohol, ethylene glycol, low molecular weight polyethylene glycols, and glycerin;

fatty acid esters such as ethyl acetate, butyl acetate, glycerin monoacetate, glycerin diacetate, glycerin triacetate, glycerin monomethacrylate, glycerin dimethacrylate, and glycerin monostearate;

aliphatic hydrocarbons, such as butane, pentane, and hexane;

aromatic hydrocarbons, such as benzene, toluene, and xylene;

ketones, such as methyl ethyl ketone and acetone;

ethers, such as diethyl ether;

alkyl halides, such as dichloromethane, chloroform, and carbon tetrachloride;

organopolysiloxanes such as dimethyl polysiloxane and divinyl dimethyl polysiloxane; and methacrylate esters, such as methyl methacrylate, ethylene glycol dimethacrylate, and hydroxyethyl methacrylate.

It is preferred that glycerin, glycerin monoacetate, glycerin diacetate, glycerin triacetate, glycerin monomethacrylate, glycerin dimethacrylate, and glycerin monostearate, or derivatives thereof are used. These organic solvents may also be used in a combination of two or more kinds.

The component (2): organic solvent is preferably contained at 10.0% to 25.0% by mass, more preferably 13.0% to 20.0% by mass, still more preferably 15.0% to 20.0% by mass, and most preferably 16.0% to 18.0% by mass based on the total mass of the ion sustained-release dental hydraulic temporary sealing material composition. When the content of the component (2) becomes less than 10.0% by mass, the paste before setting becomes very hard and its operativity upon filling in cavities or root canals becomes not only poor, and but also it may be impossible to make a paste form of the ion sustained-release dental hydraulic temporary sealing material composition of the present invention. When the content of the component (2) exceeds 25.0% by mass, the paste before setting becomes soft and its stickiness increases, and its operativity upon filling in cavities or root canals becomes not only poor, and but also its initial setting ability may worsen.

The component (3): resin is a component which confers plasticity to the ion sustained-release dental hydraulic temporary sealing material composition of the present invention and adjusts the operativity of the paste.

Known resins may be used as the component (3) without any restrictions as long as the component (3) is soluble in the component (2): organic solvent.

By illustrating the component (3): resin, its specific examples include homopolymers and copolymers, such as vinyl acetate, vinyl chloride, acrylic acid, maleic acid, and fumaric acid, and ethylene vinyl acetate copolymers. It is preferred to use a homopolymer of vinyl acetate or vinyl chloride or a copolymer thereof. These resins may also be used in a combination of two or more kinds.

The component (3): resin is preferably contained at 3.0% to 15.0% by mass, more preferably 5.0% to 10.0% by mass, still more preferably 5.0% to 8.0% by mass, and most preferably 6.0% to 8.0% by mass based on the total mass of the ion sustained-release dental hydraulic temporary sealing material composition. When the content of the component (3) becomes less than 3.0% by mass, the plasticity of the paste before setting decreases and its operativity upon filling in cavities or root canals may become poor. When the content of the component (3) exceeds 15.0% by mass, the paste before setting becomes soft and its stickiness increases, and its operativity upon filling in cavities or root canals becomes not only poor, and but also its initial setting ability may worsen.

The component (4): ion sustained-release glass is a glass having a sustained releasability of various ions including a fluoride ion, and confers an ion sustained releasability to the ion sustained-release dental hydraulic temporary sealing material composition of the present invention. The preventive function aiming at protection of tooth substance, such as tooth substance strengthening and prevention of secondary dental caries, can be conferred especially by providing an ion sustained releasability.

The ion sustained-release glass to be used for the present invention can be used without any restrictions as long as it is a glass comprising one or more kinds of glass skeleton formation elements which form a glass skeleton, and one or more kinds of glass modifying elements which modify the glass skeleton. Elements which may be made a glass skeleton formation element or a glass modifying element with glass composition in the present invention, a so-called glass amphoteric element are included within a category of a glass skeleton formation element. By illustrating the glass skeleton formation element contained in the ion sustained-release glass, its specific examples include silica, aluminum, boron and phosphorus, and these may be used alone or in combinations. Moreover, by illustrating the glass modifying element, its specific examples include halogen elements, such as fluoride, bromine, and iodine; alkaline metal elements, such as sodium and lithium; alkaline earth metals elements, such as calcium and strontium, and this glass modifying element may be used alone or in a combination of two or more kinds. It is preferred that among them, silica, aluminum, or boron is included as the glass skeleton formation element, and fluoride, sodium, or strontium is included as the glass modifying element. Their specific examples include a silica glass containing strontium or sodium, a fluoroamino silicate glass, a fluoroborosilicate glass, and a fluoro almino borosilicate glass. Further, from the viewpoint of sustained-releasing fluoride ion, strontium ion, aluminum ion, or borate ion, a fluoro almino borosilicate glass containing sodium and/or strontium is more preferable. Its glass composition is 15% to 35% by mass of $SiO_2$, 15% to 30% by mass of $Al_2O_3$, 5% to 20% by mass of $B_2O_3$, 20% to 45% by mass of SrO, 5% to 15% by mass of F and 0% to 10% by mass of $Na_2O$ in their ranges. This glass composition can be identified by using instrumental analysis, such as elementary analysis, Raman spectrum, and fluorescence X-ray analysis, and there is no problem as long as the actual measurement by any analysis methods matches to these composition ranges.

There is no restriction in particular in production methods for these glasses, and it can be manufactured with production methods, such as a fusion method or sol-gel method. Among them, the method for manufacturing with the fusion method by using a melting furnace is preferred from an easy design for the glass composition also including selection of raw materials.

Although the ion sustained-release glass to be used for the present invention has an amorphous structure, there is no problem even if it partially includes crystalline material structure. Further, even if it is a mixture of a glass having those amorphous structures and a glass having a crystalline material structure, there is no problem. A decision whether its glass structure is amorphous or not, can be made using analytical instruments, such as X-ray diffraction analysis and a transmission electron microscope. Among them, the ion sustained-release glass to be used for the present invention has preferably an amorphous structure having a homogeneous structure since it sustained-releases various ions based on a balance relation with ion concentration in external environments.

Since a sustained-release of various ions from the ion sustained-release glass to be used for the present invention is influenced by the particle size of the glass, the particle size needs to be controlled by methods, such as wet-type or/and dry-type pulverization, classification, and sieving. Therefore, the particle size (50%) of the ion sustained-release glass to be used for the present invention is in a range of 0.01 to 100 μm without any restrictions, and it is preferably in a range of 0.01 to 50 μm, more preferably in a range of 0.1 to 5 μm, and still more preferably in a range of 0.3 to 4.0 μm. Moreover, the shape of the glass may be any shape such as spherical, platy, crushed, and scaly, and is not limited in particular, and it is preferably spherical or crushed.

Further, in order to enhance an ion sustained releasability of the ion sustained-release glass, it is a preferred aspect that the ion sustained-release glass is functionalized by surface-treating its glass surface to improve an ion sustained releasability. By illustrating the surface-treating material to be used in the surface treatment, its specific examples include surfactants, fatty acids, organic acids, inorganic acids, monomers, polymers, various coupling materials, silane compounds, metal alkoxide compounds, and partial condensates thereof. Acidic polymers and silane compounds are preferably used as the surface treating material.

A method for surface-treating the ion sustained-release glass by using the acidic polymer and silane compounds as the surface treating material, specifically, a method for surface-treating the ion sustained-release glass by the acidic polymer after coating the ion sustained-release glass with the silane compounds is illustrated below.

In an aqueous dispersion containing an ion sustained-release glass pulverized to a desired average particle size by pulverization etc., a silane compound represented by the general formula (I):

[Chemical 1]

wherein Z is RO—, X is halogen, Y is —OH, R is an organic group having a carbon number of not more than 8, n, m, or L is an integer of 0 to 4, and n+m+L=4, is mixed, and then hydrolyzed or partially hydrolyzed within the same system to obtain a silanol compound, and then this is condensed to coat the surface of the ion sustained-release glass.

The above-mentioned polysiloxane treatment method is performed simultaneously with hydrolysis and condensation of silane compounds, and the polysiloxane treatment to a glass surface within the same system. Alternatively, hydrolysis and condensation of silane compounds may, however, be performed in another system to produce low-condensate silane compounds (oligomers) and then this is mixed into the aqueous dispersion containing the ion sustained-release glass to perform a surface treatment method, and thereby it is also possible to efficiently form a polysiloxane coat on the surface of the ion sustained-release glass surface. A polysiloxane treatment method is more preferabe in which commercial low-condensate silane compounds (oligomers) is used and mixed without via a low condensation generation process. For a reason that the method is preferable, this is because it is thought that condensation takes place in three dimensions, a self-condensation predominantly advances, and thereby a uniform polysiloxane coat cannot be formed on the glass surface since there is a lot of water at the polysiloxane treatment step in the case where silane compound monomer is used.

On the one hand, when using the low-condensate silane compounds (oligomers), it is thought possible to form the polysiloxane coat in a glass surface uniformly in each unit which has the polysiloxane main chain having a length. Although the shape of these low-condensate silane compounds (oligomers) is also not restricted in particular, its straight chain shape is better than a three-dimensional shape, and condensation reactivity is more poor when its degree of polymerization is larger and thereby formation of the polysiloxane coat on the ion sustained-release glass surface becomes poor. Therefore, a preferable degree of polymerization ranges from 2 to 20, and more preferably from 2 to 6.

The polysiloxane treatment in the above-mentioned aqueous dispersion is performed under a relatively low-speed stirring state, and its temperature ranges from room temperature to 100° C., more preferably from room temperature to 50° C., and stirring time is usually from several minutes to tens of hours, and more preferably from 30 minutes to 4 hours. Stirring does not need a special method, and may be performed by using the equipment usually used in the general industry. For example, the stirrer which can stir a slurry material, such as a universal mixing stirrer, a planetary mixer, etc., may be used. If stirring temperature is a temperature to which an aqueous medium does not volatilize, i.e., a temperature below the boiling point of an aqueous medium, it may be used with no problem. It is necessary to adequately adjust the stirring time since gelling speed varies depending on influences of the kind of the silane compounds or low-condensate silane compounds or its addition amount, the kind of the glass, the particle size, and its ratio occupied in the aqueous dispersion, the kind of the aqueous medium, and its ratio occupied in the aqueous dispersion, and the like. In addition, stirring has to be continued until a gel is formed by condensation of the silane compounds or low-condensate silane compounds at least. When the stirring speed is too fast, gel structure will collapse and uniform coat will not be formed. Therefore, it is necessary to perform stirring at a low speed.

Moreover, the above-mentioned aqueous medium is composed of water and alcohol. Addition of an alcohol has a great effect of making a reduced aggregability of ion sustained-release glass in a dry process to improve deagglomerating properties. A preferable alcohol is an alcohol having a carbon number of 2 to 10. An addition of methyl alcohol having a carbon number of 1 is not preferred since its volatility is high and a lot of media may volatilize in the processing step and the formation of a uniform polysiloxane coat on a glass surface may become difficult. And, an addition of an alcohol having a carbon number of more than 10 requires a long time to perform a dry removal of the solvent since the alcohol has a high boiling point. Examples of the specific alcohol include ethyl alcohol, n-propyl alcohol, isopropyl alcohol, n-butyl alcohol, t-butyl alcohol, isobutyl alcohol, n-pentyl alcohol, isopentyl alcohol, n-hexyl alcohol, n-heptyl alcohol and n-octyl alcohol, and more preferably alcohols having a carbon number of 2 to 4, such as, ethyl alcohol, n-propyl alcohol, and isopropyl alcohol are used suitably. The addition amount of the above-mentioned alcohol is 5 to 100 parts by mass, preferably 5 to 20 parts by mass based on 100 parts by mass of water. If the addition amount exceeds 100 parts by mass, problems such as a complicated dry process will occur. The content of the glass also ranges from 25 to 100 parts by mass, and more specifically, from 30 to 75 parts by mass based on 100 parts by mass of the aqueous medium. When the content exceeds 100 parts by mass, the gelling speed by condensation is fast and thereby it is difficult to form a uniform polysiloxane coating layer, and when the content is less than 25 parts by mass, glass sediments under a stirring state or its phase separation occurs in an aqueous medium. Although the addition amount of silane compounds depends on the particle size of the glass, the addition amount of silane compounds also ranges from 0.1 to 10 parts by mass, and preferably from 0.1 to 4 parts by mass in $SiO_2$ conversion based on 100 parts by mass of the glass. When the addition amount is less than 0.1 parts by mass, there is no effect of the polysiloxane coating layer formation and it could not be deagglomerated into the primary particle and thereby aggregates. When the addition amount exceeds 10 parts by mass, it becomes what solidified material after dryness cannot be deagglomerated because of being too hard.

The system in a "gel" state is dried, and an aqueous medium is removed to solidify the gel. Dryness consists of two steps of maturing and calcination, wherein the former aims at growth of its gel structure and removal of the aqueous medium, and the latter aims at strengthening of gel structure. Since dryness does not provide distortion to gel structure and aims at removing the aqueous medium, its standing is necessary and dryness is preferably performed by using an equipment of a box type hot air dryer, etc. The maturing temperature ranges from room temperature to 100° C., and more preferably from 40° C. to 80° C. When the maturing temperature is less than the range, removal of the aqueous medium becomes insufficient, and when the maturing temperature exceeds this range conversely, an aqueous medium volatilizes rapidly and there is a possibility that a defect may occur in the gel structure or a polysiloxane coating layer may exfoliate from the glass surface. There is no problem as long as the maturing time is sufficient to remove the aqueous medium since maturing time depends on the capability of a drier, etc.

On the one hand, the calcination step is divided into two steps of temperature rising and mooring, the former temperature rising step is better to gradually rise the temperature to a target temperature for a long time and there is a possibility that a rapid temperature rising causes a crack in the gel structure since the heat conduction of a gel dispersion is poor. The latter mooring stage is for calcination at a constant temperature. The calcination temperature ranges from 100 to 350° C., and more preferably from 100 to 200° C.

The aqueous medium is removed from the gel by the dryness as described above to obtain a constricted solidified material. Although the solidified material is an aggregate of ion sustained-release glass, it is not merely an aggregate of the ion sustained-release glass, and polysiloxane formed by condensation intervenes between the boundary surfaces of each fine particle. Therefore, if this solidified material is deagglomerated into a material corresponding to the ion sustained-release glass before the polysiloxane treatment by a following process, an ion sustained-release glass is obtained in which its surface is coated with polysiloxane. The "deagglomerated into a material corresponding to ion sustained-release glass before the polysiloxane treatment" herein means that the ion sustained-release glass coated with polysiloxane is deagglomerated into a primary particle, and that a different point from the original ion sustained-release glass is that each particulate is coated with polysiloxane. In addition, as long as there is no problem, a secondary aggregate may be included. Deagglomerating of the solidified material is easily possible by applying shearing force or an impact force. The deagglomerating method may be performed, e.g., by using a Henschel mixer, a crossing rotary mixer, a super mixer, etc.

As the silane compound represented by the general formula (I), tetramethoxysilane, tetraethoxysilane, tetrapropoxysilane, tetra allyloxy silane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide(silicon oxide hydrate) and the like may be illustrated. Tetramethoxysilane and tetraethoxysilane are more specifically preferred. It is preferred that the silane compound is a condensate of the silane compound represented by the general formula (I), more preferably, low-condensate silane compounds. For example, it is the low-condensate silane compounds in which tetramethoxysilane and tetraethoxysilane are condensed by their partial hydrolysis. These compounds may be used alone or in combinations.

An organosilane compound may also be added as a part of the silane compound represented by the general formula (I) at the time of the polysiloxane treatment. By illustrating the organosilane compound, its specific examples include methyl trimethoxysilane, ethyl trimethoxysilane, methoxy tripropylsilane, propyl triethoxysilane, hexyl trimethoxysilane, vinyl trimethoxysilane, vinyl triethoxysilane, vinyl tri(β-methoxyethoxy)silane, γ-methacryloxy propyl trimethoxysilane, γ-glycidoxypropyl methoxysilane, γ-mercaptopropyl trimethoxysilane, γ-amino propyl triethoxysilane, 3-amino propyl triethoxysilane, methyl trichlorosilane, and phenyl trichlorosilane. Methyl trimethoxysilane, ethyl triethoxysilane, vinyl triethoxysilane, and phenyl trichlorosilane are especially preferred. These compounds may be used alone or in combinations. However, there is a possibility that since an organic group exists in a polysiloxane layer, this layer may receive distortion at the time of formation of the polysiloxane layer, and a problem may occur in its mechanical strength. From this reason, it is necessary to limit to its small addition. Moreover, an alkoxide compound, a halide, a hydrous oxide, a nitrate, and a carbonate of other metal may also be added as a part of the silane compounds represented by the general formula (I) at the time of the polysiloxane treatment.

The ion sustained-release glass coated with a polysiloxane obtained by the polysiloxane treatment step may be obtained as a most preferred surface-treated ion sustained-release glass of the present invention by performing an acidic polymer treatment which reacts with acidic polymer. The acidic polymer treatment may be performed by using an equipment currently generally used in the technical art as long as the equipment is a dry flow type of stirrer, and its examples include a Henschel mixer, a super mixer, and a high speed mixer. The reaction of the ion sustained-release glass in which a polysiloxane coat was formed with an acidic polymer may be performed by contacting an acidic polymer solution on the above-mentioned glass by impregnating, spraying, etc. For example, what is necessary is just to perform a dry flow of the polysiloxane-coated ion sustained-release glass to distribute the acidic polymer solution from the upper part and then to sufficiently stir it in a state where the glass flows. At this time, although the dispersion method of the acidic polymer solution does not especially have restrictions, dropping which can be distributed uniformly, or a spray method is more preferred. Moreover, it is preferred to perform the reaction at a temperature near room temperature, and when the temperature increases, the reaction of an acid reactive element and the acidic polymer will be fast, and thereby formation of an acidic polymer layer will not be uniform. After heat treatment, deagglomerating of a heat-treated material is easily possible by applying a shearing force or an impact force, and the deagglomerating method may be performed by the equipment etc. which were used for the above-mentioned reaction.

There is no problem as long as the solvent to be used for manufacture of the acidic polymer solution used for the reaction is a solvent which dissolves the acidic polymer. Examples of the solvent include water, ethanol, and acetone.

Among them, water is especially preferred, and by using water, the acidic group of the acidic polymer can be dissociated and react with the surface of the ion sustained-release glass uniformly.

The ranges of the weight average molecular weight of the polymer which is dissolved into the acidic polymer solution are 2,000 to 50,000, and preferably 5,000 to 40,000. With respect to the surface treated ion sustained-release glass processed by the acidic polymer having an weight average molecular weight of less than 2,000, its ion sustained releasability tends to become low. When the acidic polymer having a weight average molecular weight of more than 50,000 is used, the viscosity of the acidic polymer solution increases, and thereby it is difficult to perform the acidic polymer treatment. Moreover, the acidic polymer concentration occupied in the acidic polymer solution preferably ranges from 3% to 25% by mass, and more preferably from 8% to 20% by mass. When the acidic polymer concentration is less than 3% by mass, the above mentioned acidic polymer layer will become vulnerable. When the acidic polymer concentration exceeds 25% by mass, it becomes difficult to diffuse the acidic polymer in the polysiloxane layer (porous material). However, once it contacts the ion sustained-release glass, its acid-base reaction is fast, and setting starts in the reaction, and thereby problems such as causing an aggregation occurs. Moreover, the addition amount of the acidic polymer solution to the ion sustained-release glass coated with polysiloxane preferably ranges from 6 to 40 parts by mass, and more preferably from 10 to 30 parts by mass. By converting in this addition amount, it is optimal that the amount of the acidic polymer to polysiloxane-coated ion sustained-release glass is 1 to 7 parts by mass, and a water amount is 10 to 25 parts by mass.

The acidic polymer which can be used in order to form an acidic polymer reaction layer on the surface of the ion sustained-release glass coated with polysiloxane by the above-mentioned method is a copolymer or homopolymer of the polymerizable monomers having acidic groups, such as phosphoric acid residue, pyrophosphoric acid residue, thiophosphoric acid residue, carboxylic acid residue, or sulfonic acid residue as an acidic group. Examples of such polymerizable monomer include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meth)acryloyloxyethoxy carbonyl phthalic acid, 4-(meth)acryloyloxyethoxy carbonyl phthalic acid anhydride, 5-(meth)acryloyl amino pentyl carboxylic acid, 11-(meth)acryloyloxy-1,1-undecan dicarboxylic acid, 2-(meth)acryloyloxyethyldihydrogen phosphate, 10-(meth)acryloyloxydecyl dihydrogen phosphate, 20-(meth)acryloyloxyeicosyl dihydrogen phosphate, 1,3-di (meth)acryloyloxy propyl-2-dihydrogen phosphate, 2-(meth)acryloyloxyethyl phenyl phosphoric acid, 2-(meth) acryloyloxyethyl 2'-bromoethyl phosphoric acid, (meth) acryloyloxyethyl phenyl phosphonate, di(2-(meth)acryloyloxyethyl)pyrophosphate, 2-(meth)acryloyloxyethyl dihydrogen thiophosphate, and 10-(meth)acryloyloxydecyl dihydrogen thiophosphate. Among these polymers, a homopolymer or copolymer of α,β-unsaturated carboxylic acid is preferred in which an acid-base reaction with an acid reactive element is comparatively late. More preferably, it is an acrylic acidic polymer, an acrylic acid-maleic acid copolymer, and an acrylic acid-itaconic acid copolymer.

In addition, in the description, the "(meth)acryloyl" represents at least one kinds selected from "acryloyl" and "methacryloyl".

The ion sustained-release glass to be used for the present invention is characterized by sustained-releasing continuously ion species attributable to its glass composition, and the ion sustained-release glass differs from a material which temporarily releases a large quantity of ion species by dissolving metal fluoride, etc. into water. The following methods can decide whether the ion sustained-release glass has an ion sustained releasability or not.

To 100 g of a distilled water is added 0.1 g of the ion sustained-release glass. The ion sustained-release glass can be regarded as having ion sustained releasability in the case where either concentration (F1) of the ion concentration or the element concentration attributable to the ion species sustain-released in the distilled water when stirred for 1 hour and either concentration (F2) according to the ion concentration or the element concentration attributable to the ion species, such as Na, B, Al or Sr, sustain-released in the distilled water when stirred for 2 hours satisfy the relationship of the following Equation (1):
[Numerical formula 1]

$$F2 > F1 \quad \text{Equation (1)}$$

Moreover, when there are a plurality of ions sustained-released from the ion sustained-release glass, all ion concentrations or element concentrations do not need to satisfy Equation (1), and it can be presumed that the ion sustained-release glass has a sustained releasability when at least one of the ion concentrations or element concentrations satisfies Equation (1).

It is preferred that the component (4): ion sustained-release glass is contained at 0.01% to 10.0% by mass, more preferably 0.1% to 5.0% by mass, still more preferably 0.1% to 4.0% by mass, and most preferably 0.1% to 3.0% by mass based on the total mass of the ion sustained-release dental hydraulic temporary sealing material composition. When the content of the component (4): ion sustained-release glass is less than 0.01% by mass, the amounts of sustained-released ions are deficient and thereby effects such as tooth substance strengthening and secondary dental caries prevention may not be expected. When the content of the component (4) exceeds 10.0% by mass, it may have a bad influence on its initial setting ability.

Further, to the ion sustained-release dental hydraulic temporary sealing material composition of the present invention may be added additives, such as pigments, dyes, reaction adjustment agents, fillers, excipients, surfactants, and antibacterial agents, in the range which does not inhibit the effect of the present invention.

Therefore, when the above-mentioned additives are added into the ion sustained-release dental hydraulic temporary sealing material composition, the total % by mass of the above-mentioned components (1) to (4) may be less than 100% by mass.

In the ion sustained-release dental hydraulic temporary sealing material composition of the present invention, the content of each of the preferred components which express the above-mentioned feature range from:
65.0% to 85.0% by mass of component (1): a hydraulic inorganic powder;
10.0% to 25.0% by mass of component (2): an organic solvent;
3.0% to 15.0% by mass of component (3): a resin; and
0.01% to 10.0% by mass of component (4): an ion sustained-release glass, based on the total mass of the dental hydraulic temporary sealing material composition. By constituting the ion sustained-release dental hydraulic temporary sealing material composition in such content ranges, tooth substance strengthening can be expected by a sustained-release of various ions including a fluoride ion while having a high initial setting ability. Even when a defect occurs on sealability, it can be expected to prevent generation of secondary dental caries.

The content of each of the components more preferably ranges from:
70.0% to 80.0% by mass of component (1): a hydraulic inorganic powder;
13.0% to 20.0% by mass of component (2): an organic solvent;
5.0% to 10.0% by mass of component (3): a resin; and
0.1% to 5.0% by mass of component (4): an ion sustained-release glass, based on the total mass of the dental hydraulic temporary sealing material composition. By constituting the ion sustained-release dental hydraulic temporary sealing material composition in such content ranges, tooth substance strengthening can be expected by a sustained-release of various ions including a fluoride ion with good operativity while having a higher initial setting ability. Even when a defect occurs to sealability, it can be expected to prevent generation of secondary dental caries.

EXAMPLES

Although Examples and Comparative Examples of the present invention are specifically explained below, the present invention is not limited to these Examples.
(Details of Components used for Preparation of the Dental Hydraulic Temporary Sealing Material Composition)

Table 1 shows the components (1) to (4) used for preparing the dental hydraulic temporary sealing material composition in Examples and Comparative Examples. The production method of the ion sustained-release glass is as follows:
(Production Method of Ion Sustained-Release Glass 1)

Various raw materials of silica dioxide, aluminum oxide, boron oxide, sodium fluoride, and strontium carbonate were mixed uniformly by using a ball mill to prepare a material mixture. Subsequently, the material mixture was melted at 1400° C. in a melting furnace. This melt was removed from the melting furnace, and then cooled on a cold steel plate or a roll or in water to produce a glass (glass composition: $SiO_2$ 23.8% by mass, $Al_2O_3$ 16.2% by mass, $B_2O_3$ 10.5% by mass, SrO 35.6% by mass, $Na_2O$ 2.3% by mass, and F 11.6% by mass). After 4 kg of alumina ball having a diameter of 6 mm was placed in an alumina pot (internal volume 3.2 L) of a tetraplex vibrating mill, 500 g of the above-mentioned glass was fed to perform its pulverization for 40 hours, and then to obtain an ion sustained-release glass 1.
(Production Method of Ion Sustained-Release Glass 2)

The polysiloxane treatment and acidic polymer treatment as shown below were performed to obtain a surface-treated ion sustained-release glass 2. Five hundred grams of the above-mentioned ion sustained-release glass 1 and a silane compound (a low condensated material of a silane compound obtained in advance by stirring 5 g of tetramethoxysilane, 1,000 g of water, and 100 g of ethanol for 2 hours at room temperature) were fed into an universal mixing stirrer, and their mixture was stirred and mixed for 90 minutes. Subsequently, this mixture was subjected to a heat treatment at 140° C. for 30 hours to obtain a heat-treated material. The heat-treated material is then deagglomerated using a Henschel mixer to obtain a polysiloxane-coated ion sustained-release glass. To 500 g of the polysiloxane-coated ion sustained-release glass was sprayed an aqueous acidic polymer solution (polyacrylic acid solution: a polymer concentration of 13% by mass, a weight average molecular weight of 20,000; Nacalai), while stirring the glass in the Henschel mixer. Then, this was subjected to a heat-treatment (100° C., 3 hours) to obtain a surface-treated ion sustained-release glass 2.

(Production Method of Ion Sustained-Release Glass 3)

After various raw materials of silica dioxide, aluminum oxide, boron oxide, sodium fluoride, and strontium carbonate were mixed, the mixture was melted to obtain a glass (glass composition: $SiO_2$ 19.8% by mass, $Al_2O_3$ 19.8% by mass, $B_2O_3$ 11.7% by mass, SrO 35.0% by mass, $Na_2O$ 2.3% by mass, and F 11.4% by mass). After 4 kg of alumina ball having a diameter of 6 mm was placed in an alumina pot (internal volume 3.2 L) of a tetraplex vibrating mill, 500 g of the resulting glass as described above was fed to pulverize it for 10 hours. Five hundred grams of the pulverized glass and a silane compound (a low condensated material of a silane compound obtained in advance by stirring 10 g of tetramethoxysilane, 1,500 g of water, 100 g of ethanol, 70 g of methanol, and 50 g of isopropanol were stirred for 2 hours at room temperature) were fed into the universal mixing stirrer, and their mixture was stirred and mixed for 90 minutes. Subsequently, this mixture was subjected to a heat treatment at 140° C. for 30 hours to obtain a heat-treated material. The heat-treated material is then deagglomerated using a Henschel mixer to obtain a polysiloxane-coated ion sustained-release glass. To 500 g of the polysiloxane-coated ion sustained-release glass was sprayed an aqueous acidic polymer solution (polyacrylic acid solution: a polymer concentration of 13% by mass, a weight average molecular weight of 20,000; Nacalai) while stirring the glass in the Henschel mixer. Then, this was subjected to a heat-treatment (100° C., 3 hours) to obtain a surface-treated ion sustained-release glass 3.

TABLE 1

Components Used in Preparations of Examples and Comparative Examples

| | |
|---|---|
| Component (1) hydraulic inorganic powder | Calcium sulfate |
| Component (2) organic solvent | Glycerin triacetate |
| Component (3) resin | Vinyl chloride-vinyl acetate copolymer |
| Component (4) ion sustained-release glass | Ion sustained-release glass 1 Ion sustained-release glass 2 Ion sustained-release glass 3 |

The 50% particle sizes of the ion sustained-release glasses 1-3 were measured. Their ion sustained releasability also was measured to identify the conformity to Equation (1). The result was shown in Table 2. In addition, the 50% particle size and the ion sustained releasability were measured by the following methods.

(50% Particle Size of Ion Sustained-Release Glasses)

It was measured using Microtrack MT3300 manufactured by Nikkiso Co., Ltd.

(Ion Sustained Releasability of Ion Sustained-Release Glasses)

To 100 g of distilled water was added 0.1 g of an ion sustained-release glass, and after one-hour stirring, it was filtered with a syringe filter for analysis (Chromatodisk 25A, 0.2 μm of Pore Size: GL Sciences).

Element concentration attributable to each ion which was sustained-released into this solution made F1. Moreover, 0.1 g of ion sustained-release glass was similarly added to 100 g of distilled water, and after two-hour stirring, the same operation was performed, and element concentration attributable to each ion sustained-released in the solution was made F2. Fluorine were measured as fluoride ion using a fluorine ion combination electrode (Model 96-09: Orion Research Inc.) and an ion meter (Mode 1720A: Orion Research Inc.), and its value was used to be converted into an elemental fluorine concentration. In addition, 0.5 mL of TISABIII (Orion Research Inc.) was added as an ion strength-adjusting agent upon their measurements. Other elements (Na, B, Al, Sr) were calculated from the measurements using inductively-coupled-plasma emission-spectrometer (ICPS-8000: manufactured by Shimadzu Corporation).

TABLE 2

Various properties of ion sustained-release glasses

| | | | Ion sustained-release glasses | | |
|---|---|---|---|---|---|
| | | | 1 | 2 | 3 |
| 50% Particle size (μm) | | | 1.2 | 1.3 | 3.1 |
| | F1 | F | 8.9 | 21.3 | 15.5 |
| | | Na | 1.2 | 1.5 | 0.9 |
| | | B | 2.3 | 2.8 | 1.9 |
| | | Al | 0.2 | 0.1 | 0.1 |
| Element concentration (ppm) | | Sr | 9.2 | 14.6 | 9.5 |
| | F2 | F | 12.5 | 32.3 | 22.5 |
| | | Na | 1.5 | 2.3 | 1.6 |
| | | B | 2.5 | 3.7 | 3.6 |
| | | Al | 0.3 | 0.2 | 0.1 |
| | | Sr | 9.7 | 21.3 | 12.4 |
| Conformity of F2 > F1 (Equation 1) | | | yes | yes | yes |

(Preparation of Dental Hydraulic Temporary Sealing Material Compositions)

According to the compositions shown in Tables 3 to 6, each component was weighted and then kneaded and mixed with a kneading and mixing apparatus to prepare a dental hydraulic temporary sealing material composition of each of Examples and Comparative Examples. The evaluation method of the dental hydraulic temporary sealing material compositions shown in Examples and Comparative Examples are as follows:

(Initial Setting Ability of Dental Hydraulic Temporary Sealing Material Compositions)

Each of the dental hydraulic temporary sealing material compositions shown in Examples and Comparative Examples was filled in a metal ring having an inside diameter of 15 mm and a height of 3 mm to produce a specimen. This specimen was immersed in a thermostatic water bath at 37° C. such that only the bottom of the specimen is contacted with water, and after standing for each time period of 5 minutes, 10 minutes, 15 minutes, and 30 minutes, the specimen was removed from the thermostatic water bath and then its moisture was removed. A Vicat needle having a weight of 100 gf and a diameter of 1 mm were gently taken down from the upper surface of the specimen to measure the thickness of the set layer from the bottom of the specimen.

(Sustained-Released Ion Amount of Dental Hydraulic Temporary Sealing Material Compositions)

Each of the dental hydraulic temporary sealing material compositions shown in Examples and Comparative Examples was filled in a metal ring having an in inside diameter of 12 mm and a height of 1 mm to produce a specimen. The produced specimen together with the stainless steel metallic mold was immersed into 5 mL of distilled water, and stood for one week at 37° C. After one week, an ion amount sustained-released from the specimen into the distilled water was measured. Fluorine was measured as fluoride ion using a fluorine ion combination electrode (Model 96-09: Orion Research Inc.) and an ion meter (Mode 1720A: Orion Research Inc.), and its value was used to be converted into elemental fluorine concentrations. In addition, 0.5 mL of TISABIII (Orion Research Inc.) was added as an ion strength-adjusting agent upon their measurements. It is preferred that the ion amount sustained-released is not less than 1 ppm, and more preferably 5 ppm. Other elements (Na, B, Al, Sr) were calculated from the measurements using an inductively coupled plasma emission-spectrometer (ICPS-8000: manufactured by Shimadzu Corporation).

Evaluation Results of Examples 1 to 3 and Comparative Example 1

Figure 1:
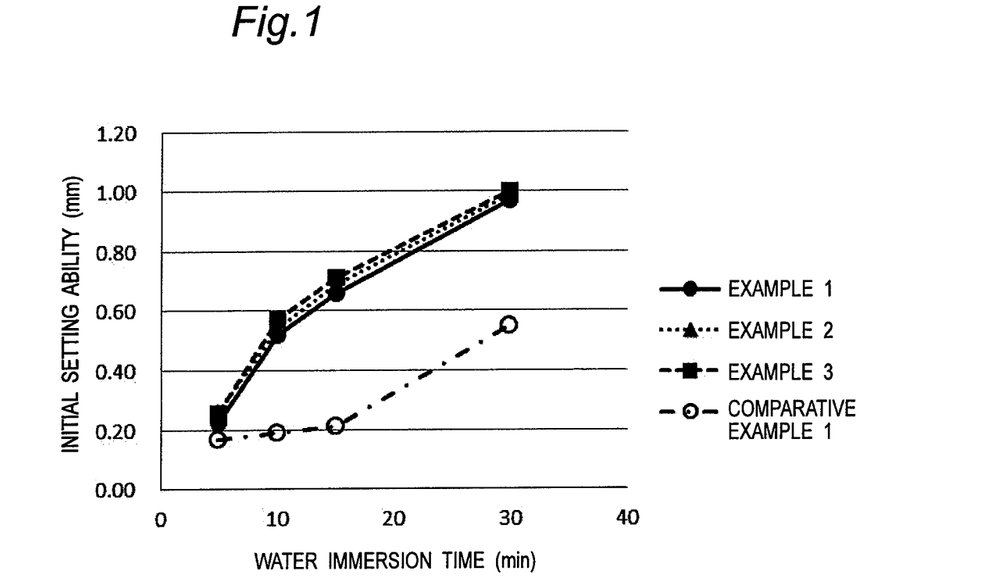
FIG. 1 is a graph indicating the initial setting ability of the dental hydraulic temporary sealing material compositions of Examples 1 to 3 and Comparative Example 1.

The evaluation results of the dental hydraulic temporary sealing material composition shown in Examples 1 to 3 and HY SEAL (manufactured by SHOFU Inc.) which is a commercial hydraulic temporary sealing material used as Comparative Example 1, were shown in Table 3 and FIG. 1.

It was recognized that Example 1 exhibited a high initial setting ability. Further, since the various ions including a fluoride ion were recognized to be sustained-released due to the content effect of the ion sustained-release glass, a protection of tooth substance, such as tooth substance strengthening and prevention of secondary dental caries, can be expected.

Example 2 is a composition prepared by substituing the kind of the component (4): ion sustained-release glass in Example 1 with the ion sustained-release glass 2.

Example 3 is a composition prepared by substituing the kind of the component (4): ion sustained-release glass in Example 1 with the ion sustained-release glass 3.

It was recognized that Examples 2 and 3 exhibited a high initial setting ability, similarly to Example 1. Further, since various ions including a fluoride ion were recognized to be sustained-released due to the content effect of the ion sustained-release glasses, a protection of tooth substance, such as tooth substance strengthening and prevention of secondary dental caries, can be expected.

Since Comparative Example 1 contains a metal fluoride, sustained-releases of fluorine ion and sodium ion could be recognized. However, sustained-releases of the other ions were less than those of Examples as compared to them, or the sustained-releases cannot be little recognized. The tooth substance protection effect such as in Examples cannot be expected. Its initial setting ability was also slow.

TABLE 3

Composition and Evaluation results of Examples 1 to 3 and Comparative Example 1

(% by mass)

| | | Example 1 | Example 2 | Example 3 | Comparative Example 1 |
|---|---|---|---|---|---|
| Component (1) hydraulic inorganic powder | Calcium sulfate | 74.00 | 74.00 | 74.00 | HY SEAL (SHOFU Inc.) |
| Component (2) organic solvent | Glycerin triacetate | 17.00 | 17.00 | 17.00 | |
| Component (3) resin | Vinyl chloride-vinyl acetate copolymer | 7.00 | 7.00 | 7.00 | |
| Component (4) ion sustained-release glass | Ion sustained-release glass 1 | 2.00 | | | |
| | Ion sustained-release glass 2 | | 2.00 | | |
| | Ion sustained-release glass 3 | | | 2.00 | |
| Total | | 100.00 | 100.00 | 100.00 | |
| Initial setting ability (mm) | after 5 min | 0.23 | 0.26 | 0.26 | 0.17 |
| | after 10 min | 0.52 | 0.54 | 0.57 | 0.19 |
| | after 15 min | 0.66 | 0.69 | 0.71 | 0.21 |
| | after 30 min | 0.97 | 0.99 | 1.00 | 0.55 |
| Ion release amount (ppm) | F | 6.3 | 15.7 | 11.2 | 7.9 |
| | Na | 7.1 | 9.9 | 6.4 | 10.5 |
| | B | 5.2 | 6.9 | 6.4 | 0.2 |
| | Al | 7.2 | 7.9 | 6.0 | 0.6 |
| | Sr | 19.5 | 44.3 | 27.4 | 18.7 |

Evaluation Results of Examples 4 to 7 and Comparative Examples 2 and 3

Figure 2:
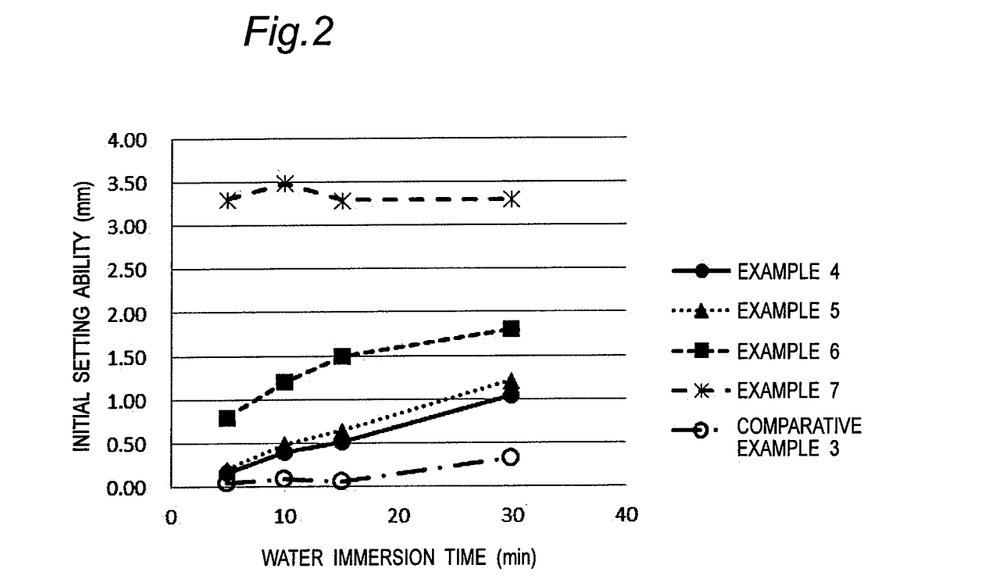
FIG. 2 is a graph indicating the initial setting ability of the dental hydraulic temporary sealing material compositions of Examples 4 to 7 and Comparative Example 3.

The evaluation results of the dental hydraulic temporary sealing material compositions shown in Examples 4-7 and Comparative Examples 2 and 3 were shown in Table 4 and FIG. 2.

Examples 4 and 5 are compositions prepared by reducing the content in the component (1): hydraulic inorganic powder and increasing the content the component (2): organic solvent and the the component (3): resin in Example 3.

Examples 6 and 7 are compositions prepared by increasing the content in the component (1): hydraulic inorganic powder, and reducing the content of the component (2): organic solvent and the component (3): resin in Example 3.

It was recognized that Examples 4 to 7 exhibit a high initial setting ability. Further, since various ions including a fluoride ion were recognized to be sustained-released due to the content effect of the ion sustained-release glasses, tooth substance protection such as tooth substance strengthening and prevention of secondary dental caries etc. can be expected.

Comparative Example 2 is a composition prepared by increasing the content in the component (1): hydraulic inorganic powder, and reducing the content of the component (2): organic solvent and of component (3): resin in Example 3.

In Comparative Example 2, since the content of the component (1): hydraulic inorganic powder to the component (2): organic solvent and the content of component (3): resin was excess, the composition could not be made into a paste.

Comparative Example 3 is a composition prepared by reducing the content in the component (1): hydraulic inorganic powder, and increasing the content of the component (2): organic solvent and component (3): resin in Example 3.

In the Comparative Example 3, it was recognized that although various ions including a fluoride ion were sustained-released due to the content effect of ion sustained-release glass, the composition had a slow initial setting ability.

TABLE 4

Composition and Evaluation results of Examples 4 to 7 and Comparative Examples 2 and 3

(% by mass)

| | | Example 4 | Example 5 | Example 6 | Example 7 | Comparative Example 2 | Comparative Example 3 |
|---|---|---|---|---|---|---|---|
| Component (1) hydraulic inorganic powder | Calcium sulfate | 65.00 | 70.00 | 80.00 | 85.00 | 91.00 | 58.00 |
| Component (2) organic solvent | Glycerin triacetate | 23.00 | 20.00 | 13.00 | 10.00 | 5.00 | 25.00 |
| Component (3) resin | Vinyl chloride-vinyl acetate copolymer | 10.00 | 8.00 | 5.00 | 3.00 | 2.00 | 15.00 |
| Component (4) ion sustained-release glass | Ion sustained-release glass 1 | | | | | | |
| | Ion sustained-release glass 2 | | | | | | |
| | Ion sustained-release glass 3 | 2.00 | 2.00 | 2.00 | 2.00 | 2.00 | 2.00 |
| Total | | 100.00 | 100.00 | 100.00 | 100.00 | 100.00 | 100.00 |
| Initial setting ability (mm) | after 5 min | 0.16 | 0.20 | 0.80 | 3.30 | Could not be made into a paste | 0.05 |
| | after 10 min | 0.40 | 0.49 | 1.20 | 3.48 | | 0.09 |
| | after 15 min | 0.52 | 0.64 | 1.50 | 3.29 | | 0.07 |
| | after 30 min | 1.04 | 1.21 | 1.80 | 3.29 | | 0.32 |
| Ion release amount (ppm) | F | 11.9 | 11.1 | 10.1 | 8.3 | | 11.2 |
| | Na | 6.8 | 6.5 | 5.7 | 5.1 | | 6.9 |
| | B | 6.0 | 5.7 | 5.2 | 4.6 | | 5.7 |
| | Al | 6.4 | 5.8 | 5.5 | 4.9 | | 6.2 |
| | Sr | 29.8 | 27.1 | 24.0 | 22.3 | | 26.6 |

Evaluation Results of Examples 8 and 9

Figure 3:
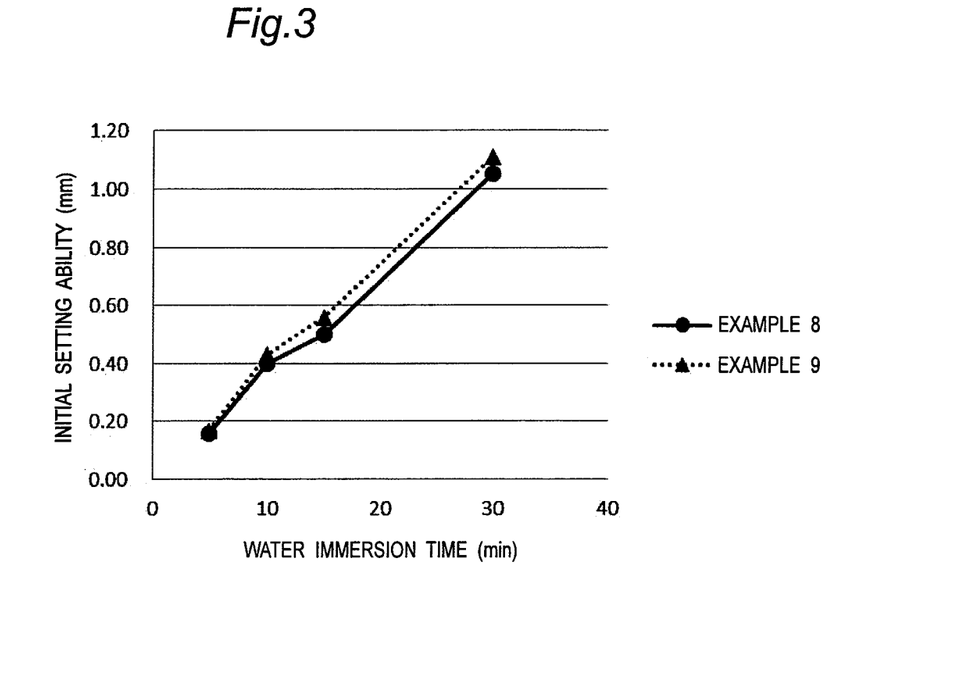
FIG. 3 is a graph indicating the initial setting ability of the dental hydraulic temporary sealing material compositions of Examples 8 and 9.

The evaluation results of the dental hydraulic temporary sealing material compositions of Examples 8 and 9 were shown in Table 5 and FIG. 3.

Example 8 is a composition prepared by increasing the content of the component (2): organic solvent, and reducing the content of component (3): resin in Example 4.

Example 9 is a composition prepared by reducing the content of the component (2): organic solvent, and increasing the content of component (3): resin in Example 4.

It was recognized that Example 8 and 9 exhibit a high initial setting ability. Further, since various ions including a fluoride ion were recognized to be sustained-released due to the content effect of ion sustained-release glasses, tooth substance protection such as tooth substance strengthening and prevention of secondary dental caries etc. can be expected.

TABLE 5

Composition and Evaluation results of Examples 8 and 9

|  |  | Example 8 | Example 9 |
|---|---|---|---|
| Component (1) hydraulic inorganic powder | Calcium sulfate | 65.00 | 65.00 |
| Component (2) organic solvent | Glycerin triacetate | 25.00 | 18.00 |
| Component (3) resin | Vinyl chloride-vinyl acetate copolymer | 8.00 | 15.00 |
| Component (4) ion sustained-release glass | Ion sustained-release glass 1 | | |
| | Ion sustained-release glass 2 | | |
| | Ion sustained-release glass 3 | 2.00 | 2.00 |
| Total | | 100.00 | 100.00 |
| Initial setting ability (mm) | after 5 min | 0.16 | 0.17 |
| | after 10 min | 0.40 | 0.43 |
| | after 15 min | 0.50 | 0.56 |
| | after 30 min | 1.05 | 1.11 |
| Ion release amount (ppm) | F | 12.1 | 11.6 |
| | Na | 6.8 | 6.5 |
| | B | 6.4 | 5.9 |
| | Al | 6.5 | 6.4 |
| | Sr | 30.0 | 27.9 |

Evaluation Results of Examples 10 to 13 and Comparative Examples 4 and 5

Figure 4:
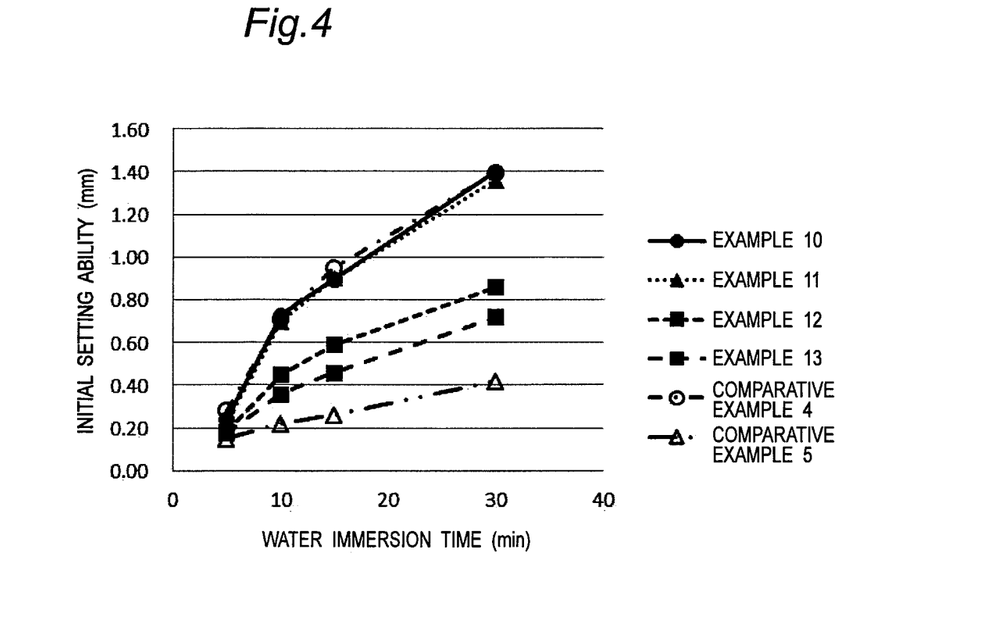
FIG. 4 is a graph indicating the initial setting ability of the dental hydraulic temporary sealing material compositions of Examples 10 to 13 and Comparative Examples 4 and 5.

The evaluation results of the dental hydraulic temporary sealing material compositions of Examples 10 to 13 and Comparative Examples 4 and 5, were shown in Table 6 and FIG. 4.

Examples 10 and 11 are compositions prepared by increasing the content in the component (1): hydraulic inorganic powder, and reducing the content of the component (4): ion sustained-release glass in Example 3.

Example 12 is a composition prepared by reducing the content in the component (1): hydraulic inorganic powder, and increasing the content of the component (4): ion sustained-release glass in Example 3.

Example 13 is a composition prepared by reducing the contents of the component (1): hydraulic inorganic powder, the component (2): organic solvent and the component (3): resin, and increasing the content of the component (4): ion sustained-release glass in Example 3.

It was recognized that Examples 10 to 13 exhibit a high initial setting ability. Further, since various ions including a fluoride ion were recognized to be sustained-released due to the content effect of ion sustained-release glass, tooth substance protection such as tooth substance strengthening and prevention of secondary dental caries etc. can be expected.

Comparative Example 4 is a composition which does not contain the component (4): ion sustained-release glass. Although it was recognized that Comparative Example 4 exhibited a high initial setting ability, it was not recognized that various ions including a fluoride ion were sustained-released. Therefore, its tooth substance protection cannot be expected.

Comparative Example 5 is a composition prepared by reducing the content of the component (1): hydraulic inorganic powder, the component (2): organic solvent and the component (3): resin, and increasing the content of the component (4): ion sustained-release glass in Example 3.

It was recognized that although in Comparative Example 5, various ions including a fluoride ion were sustained-released due to the content effect of ion sustained-release glass, the composition had a slow initial setting ability.

TABLE 6

Composition and Evaluation results of Examples 10 to 13 and Comparative Examples 4 and 5

|  |  | Example 10 | Example 11 | Example 12 | Example 13 | Comparative Example 4 | (% by mass) Comparative Example 5 |
|---|---|---|---|---|---|---|---|
| Component (1) hydraulic inorganic powder | Calcium sulfate | 75.99 | 75.90 | 71.00 | 70.00 | 76.00 | 65.50 |
| Component (2) organic solvent | Glycerin triacetate | 17.00 | 17.00 | 17.00 | 15.00 | 17.00 | 14.00 |
| Component (3) resin | Vinyl chloride-vinyl acetate copolymer | 7.00 | 7.00 | 7.00 | 5.00 | 7.00 | 5.50 |
| Component (4) ion sustained-release glass | Ion sustained-release glass 1 | | | | | | |
| | Ion sustained-release glass 2 | | | | | | |
| | Ion sustained-release glass 3 | 0.01 | 0.10 | 5.00 | 10.00 | 0.00 | 15.00 |
| Total | | 100.00 | 100.00 | 100.00 | 100.00 | 100.00 | 100.00 |
| Initial setting ability (mm) | after 5 min | 0.24 | 0.22 | 0.18 | 0.18 | 0.28 | 0.15 |
| | after 10 min | 0.73 | 0.70 | 0.45 | 0.36 | 0.71 | 0.22 |

TABLE 6-continued

Composition and Evaluation results of Examples 10 to 13 and Comparative Examples 4 and 5

|  |  | Example 10 | Example 11 | Example 12 | Example 13 | Comparative Example 4 | (% by mass) Comparative Example 5 |
|---|---|---|---|---|---|---|---|
|  | after 15 min | 0.90 | 0.90 | 0.59 | 0.46 | 0.95 | 0.26 |
|  | after 30 min | 1.40 | 1.36 | 0.86 | 0.72 | 1.40 | 0.42 |
| Ion release | F | 2.0 | 2.7 | 13.9 | 18.2 | 0.4 | 20.9 |
| amount (ppm) | Na | 3.8 | 3.9 | 8.6 | 17.3 | 4.1 | 21.0 |
|  | B | 0.8 | 1.0 | 12.0 | 25.0 | 0.0 | 31.8 |
|  | Al | 2.2 | 3.4 | 7.0 | 8.1 | 0.9 | 8.7 |
|  | Sr | 5.9 | 11.5 | 33.2 | 43.8 | 1.6 | 47.2 |

INDUSTRIAL APPLICABILITY

According to the present invention, an ion sustained-release dental hydraulic temporary sealing material composition can be provided on which a protection of tooth substance, such as tooth substance strengthening and control of secondary dental caries, can be expected by sustained-releasing various ions including a fluoride ion, while having a high initial setting ability.

The invention claimed is:

1. A dental hydraulic temporary sealing material composition consisting of:
   65.0% to 85.0% by mass of component (1): a hydraulic inorganic powder;
   10.0% to 25.0% by mass of component (2): an organic solvent;
   3.0% to 15.0% by mass of component (3): a resin;
   0.01% to 10.0% by mass of component (4): an ion sustained-release glass, and
   at least one additive selected from the group consisting of a pigment, a dye, a reaction adjustment agent, a filler, and an antibacterial agent,
   wherein the ion sustained-release glass is coated by a silane compound represented by formula (I):

(I)

wherein Z is RO—, X is halogen, Y is —OH, R is an organic group having a carbon number of not more than 8, n, m, or L is an integer of 0 to 4, and n+m+L=4,
wherein the addition amount of the silane compound ranges from 0.1 to 10 parts by mass in $SiO_2$ conversion based on 100 parts by mass of the ion sustained-release glass,
wherein the hydraulic inorganic powder is calcium sulfate, and
wherein the resin is a vinyl chloride-vinyl acetate copolymer.

2. The dental hydraulic temporary sealing material composition according to claim 1, wherein the component (4): ion sustained-release glass sustained-releases at least a fluoride ion.

3. The dental hydraulic temporary sealing material composition according to claim 1, wherein the component (4): ion sustained-release glass sustained-releases a fluoride ion, and further sustained-releases one or more kinds of bivalent to tetravalent ions.

4. The dental hydraulic temporary sealing material composition according to claim 1, wherein the component (4): ion sustained-release glass sustained-releases a fluoride ion, and further sustained-releases at least one ion selected from the group consisting of strontium ion, aluminum ion, and borate ion.

5. The dental hydraulic temporary sealing material composition according to claim 1, wherein the component (4): the ion sustained-release glass sustained-releases at least a fluoride ion, a strontium ion, and a borate ion.

6. The dental hydraulic temporary sealing material composition according to claim 1, wherein the component (2): organic solvent is glycerin or a derivative thereof.

7. The dental hydraulic temporary sealing material composition according to claim 1, wherein the component (2): organic solvent is glycerin triacetate.

8. The dental hydraulic temporary sealing material composition according to claim 1, wherein the component (2): organic solvent is glycerin triacetate, and the component (4): ion sustained-release glass sustained-releases a fluoride ion and further sustained-releases at least one ion selected from the group consisting of strontium ion, aluminum ion, and borate ion.

9. The dental hydraulic temporary sealing material composition according to claim 1, wherein the component (2): organic solvent is glycerin triacetate, and the component (4): ion sustained-release glass sustained-releases a fluoride ion and further sustained-releases at least one ion selected from the group consisting of sodium ion, strontium ion, aluminum ion, and borate ion.

10. The dental hydraulic temporary sealing material composition according to claim 1, wherein the component (4): ion sustained-release glass sustained-releases a fluoride ion, and further sustained-releases at least one ion selected from the group consisting of sodium ion, strontium ion, aluminum ion, and borate ion.

* * * * *